United States Patent [19]

Evans

[11] Patent Number: 5,474,060
[45] Date of Patent: Dec. 12, 1995

[54] FACE MASK WITH GAS SAMPLING PORT

[76] Inventor: David Evans, 16 Wells Hill Avenue, Toronto, Ontario M5R 3A6, Canada

[21] Appl. No.: 110,515

[22] Filed: Aug. 23, 1993

[51] Int. Cl.⁶ .................... A61M 16/00; A62B 7/10; A62B 18/02; F16K 31/02
[52] U.S. Cl. .................. 128/204.22; 128/205.25; 128/205.12; 128/206.12; 128/206.21
[58] Field of Search .................. 128/716, 719, 128/730, 202.27, 206.21, 206.24, 206.28, 207.12, 207.13, 912, DIG. 26, 207.18, 718, 205.25, 204.22, 205.12, 206.12

[56] References Cited

U.S. PATENT DOCUMENTS

| | | | |
|---|---|---|---|
| 1,632,449 | 6/1927 | McKesson | 128/207.13 X |
| 1,926,027 | 9/1933 | Biggs | 128/206.22 |
| 2,012,441 | 8/1935 | Willson et al. | |
| 2,104,016 | 1/1938 | Biggs | 128/206.29 |
| 2,248,477 | 7/1941 | Lombard | 128/205.25 |
| 2,484,217 | 10/1949 | Gardenier | 128/719 |
| 2,625,155 | 1/1953 | Engelder | 128/206.24 |
| 2,795,223 | 6/1957 | Stampe | 128/730 |
| 2,843,122 | 7/1958 | Hudson | 128/207.13 |
| 2,859,748 | 11/1958 | Hudson | 128/207.13 |
| 3,395,701 | 8/1968 | Bartlett, Jr. et al. | 128/719 |
| 3,880,591 | 4/1975 | Burroughs | 128/719 X |
| 4,201,205 | 5/1980 | Bartholomew | 128/205.25 |
| 4,258,710 | 3/1981 | Reber | 128/204.13 |
| 4,312,339 | 1/1982 | Thompson . | |
| 4,328,797 | 5/1982 | Rollins et al. . | |
| 4,506,665 | 3/1985 | Andrews et al. . | |
| 4,580,556 | 4/1986 | Kondur | 128/206.28 |
| 4,807,617 | 2/1989 | Nesti . | |
| 4,838,258 | 6/1989 | Dryden et al. | 128/204.18 |
| 4,997,217 | 3/1991 | Kunze | 285/387 |
| 5,005,571 | 4/1991 | Dietz | 128/205.25 |
| 5,018,519 | 5/1991 | Brown . | |
| 5,046,491 | 9/1991 | Derrick | 128/200.24 |
| 5,062,420 | 11/1991 | Levine | 128/204.18 |
| 5,063,938 | 11/1991 | Beck et al. | 128/724 |
| 5,143,061 | 9/1992 | Kaimer | 128/206.24 |
| 5,195,528 | 3/1993 | Hok | 128/716 |
| 5,195,529 | 3/1993 | Malkamäki | 128/716 |
| 5,400,781 | 3/1995 | Davenport | 128/206.28 |

FOREIGN PATENT DOCUMENTS

| | | | |
|---|---|---|---|
| 3821154 | 10/1989 | Germany | 128/912 |
| 4127599 | 2/1993 | Germany | 128/719 |
| 123579 | 2/1919 | United Kingdom | 128/206.28 |

*Primary Examiner*—Kimberly L. Asher
*Attorney, Agent, or Firm*—Weldon F. Green

[57] ABSTRACT

This invention relates to face masks, and particularly respiratory face masks for administering a gas, such as oxygen or a mixture thereof, to a patient, and specifically when an operation is performed involving a local anaesthetic or when a patient is recuperating in an intensive care unit or post-anaesthetic care unit. The face mask includes a body adapted to cover at least the nose of a wearer, and having a peripheral edge for substantially sealing at least a portion of the body of the mask to the face of a wearer. Moreover, the peripheral edge is contoured to extend over the bridge of the nose and well below the level of the eyes of the patient or wearer. The face mask includes an inlet for directing a flow of gas to the interior of the mask, and a port for allowing the exhaled air stream by the patient to flow therethrough, and particularly to a tube for directing such flow to suitable monitoring apparatus for measuring the components thereof, such as a mass spectrometer or capnograph. The port includes a connector having a configuration for releasably engaging one end of the tube presented thereto, with such connector including a conduit, and, in the preferred embodiment, in the term of a tubular portion or element, for directing the flow of gas from the interior of the mask to such tube.

6 Claims, 2 Drawing Sheets

FACE MASK WITH GAS SAMPLING PORT

FIELD OF THE INVENTION

This invention relates to the field of respiratory face masks, and more specifically to those masks which are used to administer a suitable gas, such as oxygen or a mixture thereof, to a patient, and particularly while an operation is performed involving a local anaesthetic or while a patient is recuperating in an intensive care unit or post-anaesthetic care unit.

BACKGROUND OF THE INVENTION

Generally, when a patient is under a local anaesthetic it is desirable to monitor oxygen and carbon dioxide levels in the exhaled air. This is done by providing a small tubular element or conduit leading from within the respiratory face mask and through same to its exterior, and thereby directing a portion of the stream of air exhaled by the patient to a suitable apparatus for measuring the components thereof, such as a mass spectrometer or capnograph.

It is the current practice of the profession to pierce the face mask with a needle catheter in a region thereof so as to intersect the stream of exhaled air by the patient within the mask, which catheter is provided externally with a length of suitable tubing to conduct the exhaled air stream to the monitoring apparatus.

One disadvantage of this procedure can be readily appreciated; the catheter needle could inflict injury to the operating staff during the insertion or withdrawal process or otherwise, and to the patient as well.

Further, such needle-related injuries could be of particular concern to both medical staff and patients because of the possibility of the transmission of disease through any inflicted wound.

Other proposals have been put forward for utilizing a tube or conduit length with a respiratory face mask, such as by the method disclosed in U.S. Pat. No. 4,328,797. The invention disclosed by this patent, however, primarily deals with the introduction of a length of tube through the mask to be used for naso-gastric intubation procedures.

One disadvantage of such aforementioned proposal, if it were to be used for monitoring exhaled air, is that it does not contemplate or provide for precise placement of the tube end near the nostril of the patient and in a region for repeated requisite sampling of the exhaled air stream so as to obtain an accurate measurement of the oxygen and carbon dioxide levels therein.

Another disadvantage of the aforementioned respiratory face masks, is that the body of the face mask, when located on the face of the patient or wearer, extends over the nose to a region just below the level of the wearer's eyes. This is most unaccommodating to the variety of facial features of typical patients requiring use of such respiratory face masks, and in certain circumstances, the extreme forward end of the face mask impinges on the respective corners of the eyes of the patients.

OBJECTS OF THE INVENTION

It is the principal object of this invention to provide an improved method and apparatus for use in association with a respiratory face mask so that proper and repeated samplings of an exhaled air stream by a patient can be taken to provide an accurate measurement of the oxygen and carbon dioxide levels therein.

More particularly, it is an object of this invention to provide a safe, quick, and reliable alternative to the current practice of piercing a mask with a catheter needle, to eliminating the risk of injury to both medical staff and patients during operations using the respiratory face mask of this invention, and particularly involving local anaesthetics.

It is a further object of this invention to provide a simple, yet cost effective procedure for connecting an end of a connecting tube to the respiratory face mask.

Moreover, it is an object of this invention to provide a mask which is both effective, yet comfortable to a patient or wearer, particularly when the wearer is conscious, such as those operations involving a local anaesthetic.

FEATURES OF THE INVENTION

It is therefore a feature of this invention to provide an improved respiratory face mask for administering a gas having a body adapted to cover at least the nose of a wearer and having a peripheral edge to seal at least a portion of the body of the face mask to the wearer. The face mask includes an aperture for directing a flow of gas, typically oxygen or a mixture thereof, to the interior of the mask, as well as a port formed in the body for allowing gas to flow therethrough.

It is a feature of this invention to provide a connector which is presented by the port and has a configuration for releasably engaging an end of a tube presented thereto and including a conduit for directing a flow of gas from the interior of the mask to such tube for repeated samplings of the exhaled air stream by the patient or wearer of the face mask to be delivered to suitable apparatus for measurement of the oxygen and carbon dioxide levels therein.

It is a feature of this invention that the conduit of the connector in the preferred embodiment, is a tubular element including a first part having a shape and configuration to fit snugly within the port, and a second part which extends from the first part outwardly and away from the body of the face mask and having a shape and configuration to releasably engage the end of the tube presented thereto.

It is a further feature of this invention that the hollow body includes a sealing member having a shape and configuration to cooperate with the port to prevent the transfer of gas between the first part of the tubular element and the port. Particularly the sealing member is presented between the first part and the second part of the tubular element and is of a shape and configuration to abut the exterior surface of the body of the mask around the port.

In order to adequately secure the connector to the respiratory face mask it is a feature of this invention that the first part of the tubular element of the connector extend through the port and beyond the interior surface of the body of the mask. An engaging means or boss is secured to that portion of the first part extending into the interior of the face mask and, in the preferred embodiment, abuts the interior surface of the body of the mask opposite to where the sealing member abuts the exterior surface of the mask to secure the tubular element of the connector to the mask and prevent the transfer of gas between the first part of the tubular element and the port.

It is a further feature of this invention that the tubular element of the connector includes a third part extending from the first part and further projecting into the interior of the body of the respiratory face mask to the region of the nostril of a patient or wearer of the mask. This enhances the quality of the repeated samplings of the exhaled air stream by the patient or wearer of the face mask for delivery to suitable apparatus for measuring of oxygen and carbon dioxide levels therein.

Moreover, it is a feature of this invention that the first, second, and third parts of the tubular element are all cylindrical in configuration; the third part, in the preferred embodiment, has a diameter less than that of the first part.

It is also a feature of this invention that the second part of the connector includes a threaded end having a shape and configuration to releasably engage a complimentary threaded end provided on an end of the tube presented thereto. This threaded connection provides quick, reliable, and safe releasable connection or engagement of the tube to the tubular element of the connector provided in the body of the face mask for directing repeated samplings of the exhaled air stream by the patient or wearer to suitable apparatus for measurement.

It is also a feature of this invention to have the peripheral edge of the face mask contoured to fit over the bridge, or just below the bridge, of the nose of a patient or wearer, and well below the level of the eyes.

Moreover, the body of the mask in the region where the peripheral edge is contoured to fit over the bridge, or just below the bridge, of the nose includes, projecting from its interior surface thereof, a cushion for presentation to the nose of the patient or wearer. In the preferred embodiment, this cushion comprises a felt strip.

It is also a feature of this invention to provide a method for releasably connecting a tube to a port presented in the body of a face mask for administering a gas and including a connector, presented by the port and having a configuration for releasably engaging one end of the tube presented thereto, and with the connector including a conduit for directing a flow of gas from the interior of the mask to such tube. The method includes the steps of:

securing the face mask to the face of a wearer such that the peripheral edge of the face mask substantially seals at least a portion of the body of the mask to the face of the patient or wearer;

bringing an end of the tube into contact with the connector presented by the port in the body of the face mask; and effecting the releasable connection so that the conduit of the connector directs a flow of gas from the interior of the mask to such tube.

Moreover, it is a feature of this invention that the method includes a tubular element having a first part of a shape and configuration to fit snugly within the port, a second part extending from the first part outwardly and away from the body of the mask and of a shape and configuration to releasably engage the end of the tube presented thereto.

It is also a feature of this invention that the second part of the tubular element of the connector includes a threaded means, and that the tube includes a complementary threaded means provided on the end presented to the connector for effecting the releasable connection of the tube to the connector.

DESCRIPTION OF THE DRAWINGS

These and other objects and features will become apparent in the following description of the preferred embodiment of the invention to be read in conjunction with the accompanying sheets of drawings in which.

DESCRIPTION OF THE PREFERRED EMBODIMENT

Figure 1:
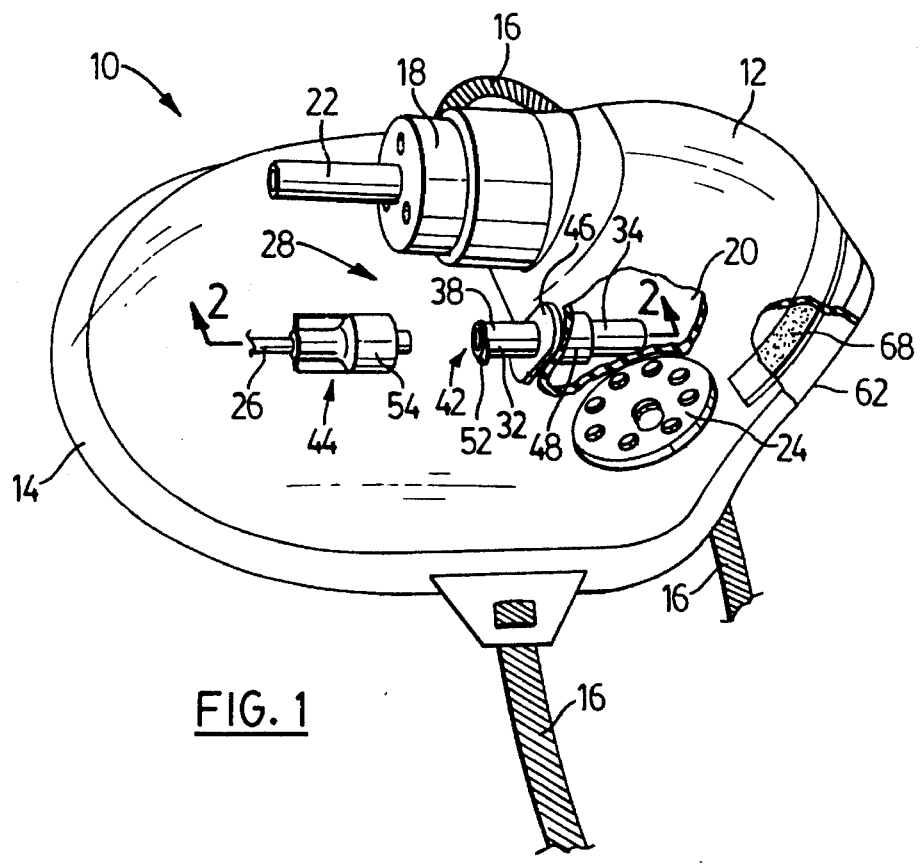
FIG. 1 is a perspective view of a respiratory face mask modified in accordance with this invention to provide a contoured peripheral edge and to present a connector including a tubular element or conduit within the body of such face mask to provide for ready connection of the tubular element or conduit to a tube for directing a portion of the exhaled air stream by the patient from the interior of the face mask to suitable monitoring apparatus.
Figure 3:
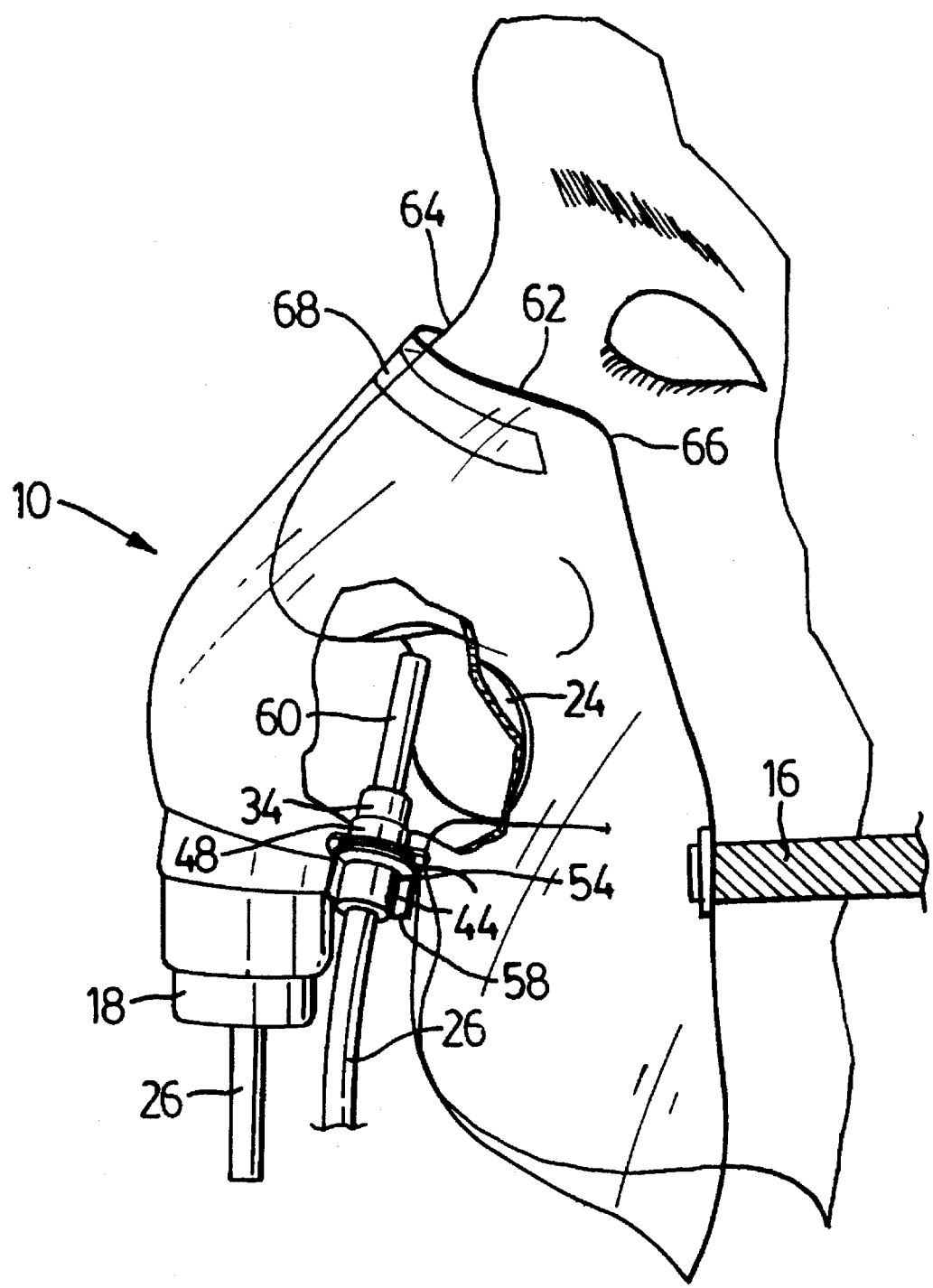
FIG. 3 is a perspective view of the respiratory face mask of this invention illustrating use with a patient, and particularly illustrating the fitting of the mask featuring a contoured peripheral edge to a patient, as well as the location of the tubular element into the interior of the face mask and in the vicinity of the nostril of the patient for repeated samplings of the exhaled air stream for delivery to suitable apparatus for measuring the oxygen and carbon dioxide levels therein.

FIG. 1 shows a respiratory face mask 10 used to administer a suitable gas, such as oxygen or a mixture thereof, to a patient, and particularly when operations are performed involving local anaesthetics or when patients are recuperating in intensive care units or post-anaesthetic care units. Respiratory face mask 10 suitably contoured includes a body portion 12 having a peripheral edge formation 14 for placement over the nose and mouth of a wearer or patient (see FIG. 3), and a strap 16 to secure mask 10 to the wearer. It can be appreciated that peripheral edge formation 14 should have a configuration which seals mask 10 against the facial tissue of the patient or wearer, and particularly around the region of the nose or the nose and mouth of the wearer. The peripheral edge formation is also contoured to provide a more comfortable fit around the nose of a patient or wearer, as best illustrated in FIG. 3 and as will hereinafter explained.

Face mask 10 includes first port or inlet formation 18 through which a suitable gas, usually oxygen or a mixture thereof, is delivered to interior 20 of face mask 10 via inlet tube 22.

During normal operation excess gas and air exhaled by the patient are vented to the outside atmosphere through suitably placed side vents 24.

Such a respiratory face mask as described (except for the contoured peripheral edge) is typical in the industry, in common use, and of a construction which is well known.

It can be appreciated that during operations involving local anaesthetics it is desirable to monitor the exhaled air stream from a patient and deliver a portion of such exhaled air stream to proper monitoring apparatus such as a mass spectrometer or capnograph (not illustrated). This is typically accomplished through connecting a tube 26 from the monitoring apparatus to face mask 10 and preferably to a location on body 12 of face mask 10 to optimize the repeated samplings taken of the exhaled air stream by the patient or wearer of the face mask so that an accurate measurement of the oxygen and carbon dioxide levels therein is accomplished.

As hereinbefore mentioned this connection to face mask 10 is currently accomplished through using a catheter needle which pierces the body of face mask 10 in a selected region to intersect the stream of exhaled air by the patient within the mask. This invention, however, provides a quick, safe, and reliable alternative for withdrawing a portion of the stream of exhaled air by the patient from within the respiratory face mask to tube 26 in the form of a conduit formation 28.

In order to use the conduit formation of this invention face mask 10 as currently used must be modified to include a port 30 in body portion 12 of the face mask, and preferably in such a location to optimize repeated samplings of exhaled air by the patient.

Conduit formation 28 of this invention includes a tubular portion or element 32 having a shape and configuration to fit within port 30 provided in body 12 of face mask 10, and in the preferred embodiment, tubular portion or element 32 of connector 28 is cylindrical in shape and configuration.

Tubular portion or element 32 extends within and through port 30 so that a first part 34 thereof extends beyond interior surface 36 of body 12 of face mask 10 and into interior 20 of such mask, while a second part 38 thereof extends beyond exterior surface 40 of body 12 of face mask 10 so that an end 42 is presented by tubular portion or element 28 for releasable engagement with an adaptor 44 presented by tube 26, as will hereinafter be explained.

Figure 2:
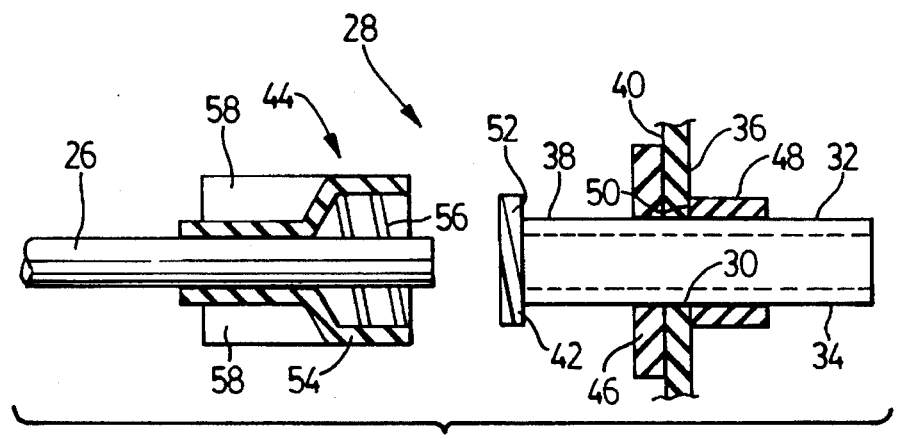
FIG. 2 is a cross sectional view taking along the lines 2—2 in FIG. 1 illustrating in detail the structure of the connector of this invention.

Tubular portion or element 32 of connector 28 presents, approximately intermediately of its longitudinal extent thereof, a flange 46 extending therearound, and which rests or abuts against exterior surface 40 of body 12 of face mask 10 when tubular portion or element 32 of connector 28 is fitted within port 30, as best illustrated in FIG. 2. Flange 46 both seals and supports the orientation of tubular portion or element 32 within port 30.

It can be appreciated that maintaining the orientation of tubular portion or element 32 within port 30 is important to ensure that optimum repeated samplings of exhaled air by the patient is maintained when face mask 10 is used during operations involving local anaesthetics, or while the patient is recovering in the intensive care unit, or post-anaesthetic unit. In particular, and as illustrated in FIG. 3, it is desired that first part 34 of tubular portion or element 32 be orientated so that the end of same is in the region of the nostril of the patient or wearer of face mask 10 and maintained in such position to optimize the repeated samplings of exhaled air by the patient for delivery to the monitoring apparatus.

Similarly, optimum samplings of exhaled air from the patient are maintained by having flange 46 provide a seal between first part 34 of tubular portion or element 32 and port 30 within body 12 of face mask 10 preventing air from the outside environment from transferring or leaking into interior 20 of face mask 10 and contaminating the repeated samplings of the exhaled air stream by the patient.

First part 34 of tubular portion or element 32 which extends beyond interior surface 36 of body 12 of face mask 10 and into interior 20 thereof features a boss 48 of a complementary cylindrical shape and configuration to fit snugly over first part 34 so that edge 50 thereof engages interior surface 36 of body of face mask 10 opposite to where flange 46 engages exterior surface 40 of body 12 of face mask 10 to firmly secure and support tubular portion or element 32 within port 30 in body 12.

In construction, then, port 30 is perforated or punched out of body 12 to receive tubular portion or element 32 of connector 28. A solvent is applied to tubular portion or element 32 of connector 28 before insertion of such portion or element within port 30. This solvent softens and chemically welds tubular portion or element 32 within port 30 of body 12. Similarly, this solvent is applied to the surface of flange 46 which abuts against exterior wall 40 of body 12 of face mask 10 to effect chemical welding of the components over that region.

Once tubular portion or element 32 and flange 46 have been properly inserted within and through port 30 in body 12, the solvent is applied to the interior surface of boss 48 and then this is affixed over first part 34 of tubular portion or element 32 so that edge 50 of boss 48 abuts against the interior surface 36 of body 12, as described above, and opposite to where flange 46 engages exterior surface of body 12 of face mask 10. In this manner boss 48 is chemically welded to first part 34 of tubular portion or element 32 and against the interior surface 36 of the body 12 at the point of contact.

Tubular portion or element 32 and flange 46 are typically manufactured from a rigid poly vinyl chloride (PVC) material. Boss 48 is typically constructed from a soft poly vinyl chloride (PVC) material, similar to the material used in constructing face mask 10, as is well known in the art.

Solvents suitable for softening the PVC's used in constructing the tubular portion or element, flange, and boss, and to effect the appropriate chemical welding desired, are well known in the art, one being, for example, cyclohexanone.

Second part 38 of tubular portion or element 32 extending beyond exterior surface 40 of body 12 of face mask 10 preferably presents at end 42 a substantially cylindrical outer surface to which tube 26, for directing to the monitoring apparatus the repeated samplings of exhaled air from the patient, can be releasably secured.

To releasably secure tube 26 to end 42 of second part 38 of tubular portion or element 32 of connector 28 so that same can not be dislodged, it is, in the preferred embodiment, found that a threaded screw mechanism in the form of a luer lock provides efficient, quick, and safe releasable engagement, as well as provides for a releasable connection which prevents outside air from entering tube 26 at the point of connection to connector 28.

In particular, end 42 of second part 38 of tubular portion or element 32 of connector 28 presents over its outer surface an external thread 52.

Adaptor 44 presented by the end of tube 26 is of rigid poly vinyl chloride construction and features an enlarged cylindrical portion 54 having within its interior surface thereof a complimentary internal thread 56 to external thread 52 presented by end 42 of second part 38 of tubular portion or element 32. Adaptor 44 of tube 26 features wings 58 extending from the body thereof to assist the operator in rotating the cylindrical portion 54 to releasably engage internal thread 56 thereof to external thread 52 presented by second part 38 of tubular portion or element 32 of connector 28, as will be hereinafter explained.

In constructing adaptor 44 and fitting same over the end of tube 26, a solvent is preferably used, as herein before explained in the construction of tubular portion or element 32 of connector 28, and its associated flange 46 and boss 48, to chemically weld adaptor 44 to the end of tube 26. Such methods of construction are well known to those skilled in the manufacture of products made from PVC materials.

It can be appreciated that in order to optimize repeated samplings of the exhaled air stream by the patient or wearer of face mask 10, first part 34 of tubular portion or element 32 should extend into interior 20 of face mask 10 to a position adjacent the nostril of the patient or wearer of the face mask. In order to achieve this orientation and placement of first part 34, tubular portion or element 32 on body 12 of face mask 10 should be favourably located and the position illustrated in FIG. 1 has been found to be preferred. This orientation and positioning of tubular portion or element 32 on body 12 of face mask 10 will allow inlet tube 22 and tube 26 to run side-by-side in a non-interfering manner, reducing, if not eliminating, entanglement of these tubes. Of course other positioning can be used if one were to configure first part 34 of tubular portion or element 32 within interior 20 of face mask 10 so that same is brought into a region adjacent the nostril of the wearer of the face mask, yet present inlet tube 22 and tube 26 in a non-interfering arrangement.

Figure 2A:
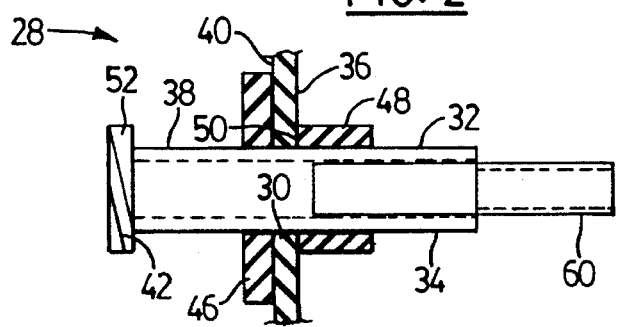
FIG. 2a is a cross sectional view similar to FIG. 2 showing an alternative embodiment of the tubular element of the connector.

It has been found that optimum repeated samplings of the exhaled air stream by the patient can be achieved if connector 28 includes an extension 60 from first part 34 of tubular portion or element 32, as particularly illustrated in FIG. 2a. This alternative embodiment extends the reach of first part 34 into interior 20 of face mask 10 and into a region adjacent the nostril of a typical patient or wearer of the face mask (see FIG. 3).

Placement of the end of first part 34 of tubular portion or element 32 in the vicinity of the nostril of the patient, either on its own or with the aid of extension 60, is preferred for optimum repeated samplings of the exhaled air stream by the patient. If this placement is not in the region of the nostril of the patient or wearer of face mask 10, then fresh oxygen, or a mixture thereof, entering the mask through inlet 18 from inlet tube 22 would mix and contaminate the exhaled air stream of the patient diluting the repeated samplings of exhaled air before delivery to the monitoring apparatus through tube 26.

During normal use of the respiratory face mask 10 of this invention, a patient is first fitted with the mask as illustrated in FIG. 3, so that body 12 of face mask 10 covers at least the nose of the patient or wearer, and peripheral edge 14 thereof substantially seals at least a portion of the body of the mask to the patient, and particularly in the region of the nose. A patient would typically be wearing respiratory face masks 10, as illustrated herein, in operations involving local anaesthetic, or if the patient is recovering in an intensive care unit or post-anaesthetic care unit.

In order to monitor the exhaled air from the patient and measure the components thereof, a tube for directing a portion of the exhaled air stream from the patient to suitable monitoring apparatus, such as a mass spectrometer or capnograph, is secured to body 12 of face mask 10 by the operator first gripping wings 58 of adaptor 44 presented by the end of tube 26 and bringing same into contact with second part 38 of tubular portion or element 32 presented by the body 12 of mask 10, and preferably presenting internal thread 56 of adaptor 44 in alignment with complementary external thread 52 presented by end 42 of second part 38 of tubular portion of element 32 of connector 28. By rotating wings 58 of adaptor 44 internal thread 56 and external thread 52 releasably engage one another in a well known manner and tube 26 is thus releasably secured to the end presented by second part 38 of tubular portion or element 32.

Once it is no longer necessary to monitor the exhaled air stream from the patient the operator grasps wings 58 of adaptor 44 and rotates same in the appropriate direction to effect release of the threaded engagement with second part 38 of tubular portion or element 32 and thus separate tube 26 from face mask 10.

It can be seen that an effective connecting means is provided maximizing safety to both medical staff as well as patients, yet is simple in its overall application and execution. In particular, the various elements of connector 28 are constructed of well known durable plastics costing a fraction of that of a typical catheter needle, the standard used in the industry today.

Respiratory face mask 10 of this invention is not only effective, it is also comfortable to a patient or wearer, particularly when the wearer is conscious, for example, during those operations involving a local anaesthetic.

In particular, respiratory face mask 10 is modified so that peripheral edge 14 of body 12 is contoured, as at 62 to fit over or just below bridge 64 of the nose of a wearer, see FIG. 3.

By contouring peripheral edge 14 of body 12 of face mask 10 as at 62, the face mask avoids the disadvantages of prior face masks, which when worn by a patient or wearer had their forward portions extending to the region just below the level of the patient's or wearer's eyes. This is them unaccommodating to many variety of facial feature types of typical patients or wearers, and in certain circumstances, the forward portions of the face mask impinge on the corners of the eyes of the patient or wearer.

In the embodiment illustrated in FIGS. 1 and 3, it can be seen that the contouring, as at 62, presents the forward portions 66 of face mask 10 well below the level of the eyes of the patient or wearer, yet still allows the body of the mask to extend over the bridge, or just below the bridge, of the nose of a patient or wearer, to effect the appropriate seal in the region of the nose of the patient or wearer, yet promote comfort and eliminate forward portions 66 of face mask 10 from impinging on the respective corners of the eyes of the patient or wearer.

Further, in order to promote comfort, the body of the mask in the region where peripheral edge is contoured as at 62, presents depending from interior surface 36 thereof, a cushion 68 for presentation to the bridge 64, or just below, of the nose of the patient or wearer. In the preferred embodiment, cushion 68 comprises a felt strip.

While specific embodiments of this invention have been illustrated and described herein, the invention is not limited to the specified constructions disclosed. Those skilled in the art may be able to provide modifications or alternatives to the disclosed structural features while still practising this invention. It is intended to cover all such modifications and alternatives as well as other embodiments not disclosed which do not constitute a departure from the spirit and scope of the attached claims.

What I claim is:

1. In a face mask for administering gas to a patient and for withdrawing a sample of exhaled gas from such patient for testing during administration, a body portion having an extent and so shaped as to overlie and enclose at least the lower region of the nose of the patient and extending therebelow and having a peripheral edge formation contoured so as to substantially seal against the surrounding facial tissue to thereby establish an interior chamber portion below the nostrils, input means associated with said body portion for directing a stream of gas from the exterior of said body portion into the chamber portion for administration to the patient and port means presented by said body portion in spaced relation to said input means, said port means including conduit means for selectively withdrawing exhaled gas for testing during gas administration extending from a region within said chamber next below a nostril of the patient to the exterior of said body portion and sealing means including an inner element and an outer element each having a shape so as to surround and support said conduit means inwardly and outwardly from said body portion and so secured thereto respectively such that orientation of said conduit means within said chamber is substantially maintained to ensure optimum repeated samplings of exhaled air.

2. A face mask according to claim 1 wherein said conduit means comprises a length of tubular element including a first part which extends from a region of said chamber next below a nostril to said body portion and a second part which extends outwardly and away from said body portion to thereby define a flow path for withdrawing exhaled gas from said region to the exterior of said body portion.

3. A face mask according to claim 2 wherein said first part of said tubular element is provided with tubular extension means at the end thereof remote from said body portion for varying the length of said flow path defined thereby.

4. A face mask according to claims 2 or 3 wherein said second part of said tubular element terminates outwardly and away from said body portion in releasable means for establishing gas flow path communication with testing apparatus.

5. A face mask according to claim 1 wherein said contoured peripheral edge formation in the region to overlie the nose of a patient includes cushioning means extending therealong.

6. A face mask according to claim 5 wherein said cushioning means comprises a felt strip.

* * * * *